United States Patent [19]

Amadera

[11] Patent Number: 4,906,187
[45] Date of Patent: Mar. 6, 1990

[54] DEVICE FOR SCALING AT THE GUM POCKET

[75] Inventor: Haruichi Amadera, Tokyo, Japan

[73] Assignee: Koichi Okano, Nagahama, Japan; a part interest

[21] Appl. No.: 226,914

[22] Filed: Aug. 1, 1988

[51] Int. Cl.[4] .............................................. A61G 17/02
[52] U.S. Cl. ........................................ 433/80; 433/85; 128/66
[58] Field of Search ................ 128/62 A, 66; 433/80, 433/81, 85, 88, 100

[56] References Cited

U.S. PATENT DOCUMENTS

| | | | |
|---|---|---|---|
| 2,757,668 | 8/1956 | Meyer-Saladin | 128/66 |
| 4,248,589 | 2/1981 | Lewis | 433/80 |
| 4,303,064 | 12/1981 | Buffa | 128/62 A |
| 4,412,402 | 11/1983 | Gallant | 433/88 |
| 4,793,807 | 12/1988 | Friedman et al. | 128/66 |

Primary Examiner—John J. Wilson
Attorney, Agent, or Firm—Finnegan, Henderson, Farabow, Garrett & Dunner

[57] ABSTRACT

A device for scaling sordes and tartars on the surface of teeth at the gum pocket having improved construction, in which there are provided a hand-piece for an ejection nozzle; a compressor for feeding pressurized air to the ejection nozzle at one end of the hand-piece; a conduit pipe for transporting the compressed air; a water sump; and a conduit for leading water from the water sump to the ejection nozzle, the compressed air being ejected from the ejecting nozzle of the hand-piece under a pressure of from 1 to 2 kg/cm$^2$ and in an ejecting quantity of from 6 to 9 l /min., and water being ejected together with the pressurized jet air in an ejecting quantity of from 10 to 30 cc/min. in the form of a spray jet.

3 Claims, 2 Drawing Sheets

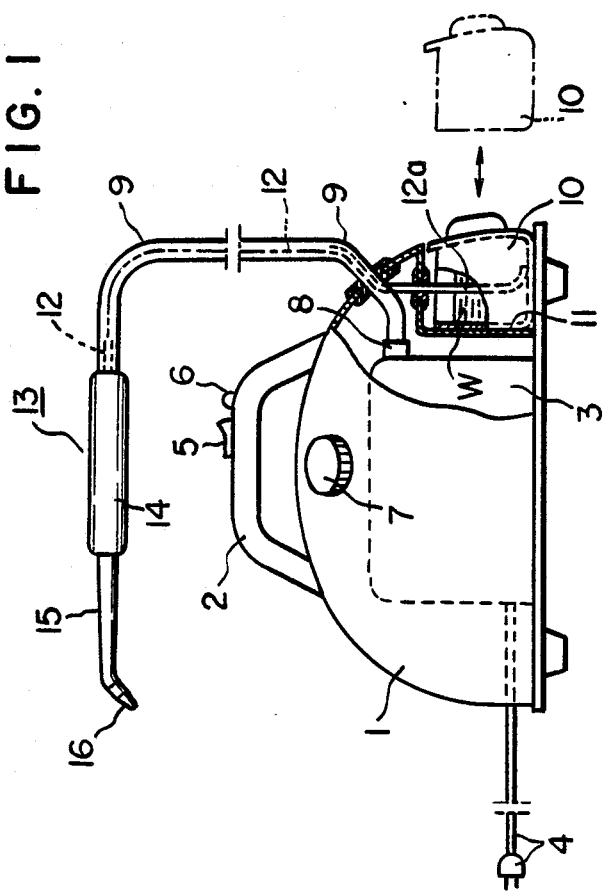
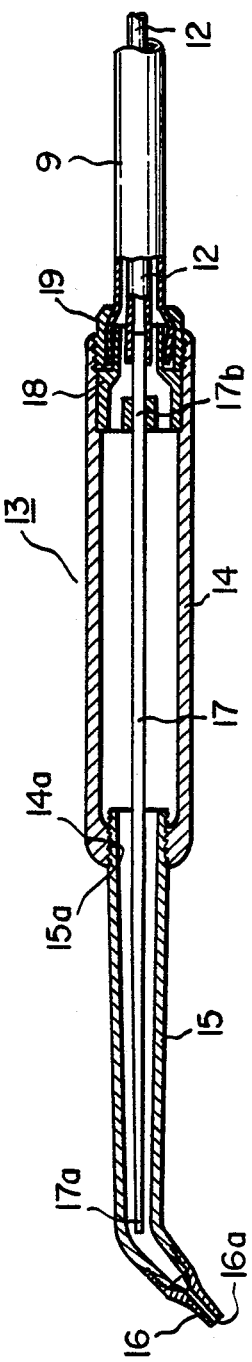

DEVICE FOR SCALING AT THE GUM POCKET

BACKGROUND OF THE INVENTION (a) Field of the Invention

This invention relates to a dental hygienic device, and, more particularly, it is concerned with a device for positively and effectively scaling and washing-out sordes (including dental calculus or tartars) on the surface of teeth at a portion which is a so-called "gum pocket" or "cul-de-sac" between a tooth and a gingival edge, and also for removing various germs (in particular, aerophobic bacteria) which are ever present in the gum pocket as well, as the consequence of which the pathological condition of the soft tissues of the teeth including the gum pocket is improved and formation of sordes and sedimentation of tartars on the surface of teeth are also suppressed, such improved conditions being able to be constantly maintained.

(b) Description of Prior Art

The sordes and tartars on the surface of teeth at the gum pocket tend to cause dental diseases such as pyorrhea alveolaris (or gum disease), etc. In view of considerably strong adhesive force of the sordes and tartars onto the surface of teeth, it is fairly difficult to remove them with a tooth brush. From the clinical standpoint of the dental surgery, it has been and is usually a practice to remove the dental calculus on the surface of teeth by inserting the tip end of a scaler into the gum pocket to scrape them off, or removing the sordes and tartars by impinging a jet stream of water onto the gum pocket through a jet nozzle for washing the oral cavity to peel them off.

However, the scraping of the tartars and sordes with use of a blade hand-piece would stimulate the dental nerves to arouse pain and disagreeableness on the treated part, or it tends to scratch the gingiva to provoke bleeding, with the further disadvantage of an inefficient and time-taking operation. Moreover, such a scaling operation cannot be controlled by a patient himself (or herself).

The removal by scraping of tartars and sordes with the use of a jet water nozzle is to remove them on the surface of teeth by directly impinging the pressurized jet water onto the surface of teeth at the gum pocket. For this purpose, it is necessary that the gingiva b at the gum pocket where the jet water is impinged be sufficiently separated from the surface of teeth a to be brought to an open state, as indicated by a double dots-and-dash line in FIG. 5 of the accompanying drawing, whereby the surface of teeth becomes exposed to the outside to enable the jet water to directly act on the sordes and tartars on the surface of the teeth. In practice, however, the gingiva b at the gum pocket does not become sufficiently separated from the surface of the tooth a to be brought to an open state, even when the jet water at a considerably high ejecting pressure is impinged on the gum pocket, hence the jet water is difficult to act effectively on the surface of the teeth at the gum pocket, where the sordes and tartars are adhered.

As the ejecting pressure of the jet water is increased to sufficiently open the gingiva b, impingement of the jet water stream to the surface of teeth a, the gingiva b, and every other part of the mouth becomes excessive to result in injury to the teeth a and the gingiva b, or causing pain and disagreeable feeling to the user. In addition, since a large quantity of water flows out of the mouth during use of the jet water nozzle, it compels the user to lean his or her body forward, approaching his or her face closer to the wash basin, etc. to handle the jet nozzle hand-piece in a very confined, slouched posture.

SUMMARY OF THE INVENTION

The present invention has been made with a view to improving the abovementioned disadvantages inherent in the conventional device, and aims at scaling sordes and tartars on the surface of teeth as well as removing germs ever present in the gum pocket with use of pressurized jet water same as done in the conventional devices.

It is therefore an object of the present invention to provide a practical device for scaling sordes and tartars on the surface of teeth at the gum pocket, which have various advantages such that (1) the jet water directly acts on the surface of teeth where sordes and tartars are adhered, in a state of the gingiva b at the gum pocket being sufficiently separated from the surface of a tooth a, so that the sordes and tartars can be effectively removed; (2) the pressure of the jet water can be relatively low, hence there is no possibility of injury caused to the teeth and the gingiva, nor giving pains and disagreeable feeling to the user; (3) the water to be used for scaling can be in a relatively small quantity; and so forth.

According to the present invention in general aspect of it, there is provide a device for scaling sordes and tartars on the surface of teeth at the gum pocket, which comprises: a hand-piece for an ejection nozzle; a compressor for feeding pressurized air to said ejection nozzle at one end of said hand-piece; a conduit pipe for transporting the compressed air; a water sump; and a conduit for leading water from said water sump to said ejecting nozzle, said compressed air being ejected from said ejection nozzle of the hand-piece under a pressure of from 1 to 2 kg/cm$^2$ and in an ejecting quantity of from 6 to 9 l/min., and water being ejected together with said pressurized jet air in an ejecting quantity of from 10 to 30 cc/min. in the form of a spray jet.

The foregoing object and other objects, as well as the construction and function of the device for scaling sordes and tartars on the surface of teeth according to the present invention, will become more apparent and understandable from the following detailed description thereof, when read in conjunction with the accompanying drawings.

BRIEF DESCRIPTION OF THE ACCOMPANYING DRAWINGS

In the drawings:

FIG. 1 is a side elevational view, partly cut away, showing the entire external appearance of one embodiment of the scaling device according to the present invention;

FIG. 2 is an enlarged view in longitudinal cross-section of the hand-piece having the ejection nozzle at its one end;

DETAILED DESCRIPTION OF PREFERRED EMBODIMENTS

In the following, the present invention will be described in specific details in reference to the accompanying drawing.

As mentioned in the foregoing, it has been the fact that, even if the jet water alone is impinged on the gum pocket at a fairly high ejecting pressure, the gingiva b at the gum pocket is not sufficiently separated from the surface of the tooth a to be brought to an open state with the consequence that such jet water is difficult to act effectively on the surface of the tooth at the gum pocket, where sordes and tartars are stuck.

Figure 5:
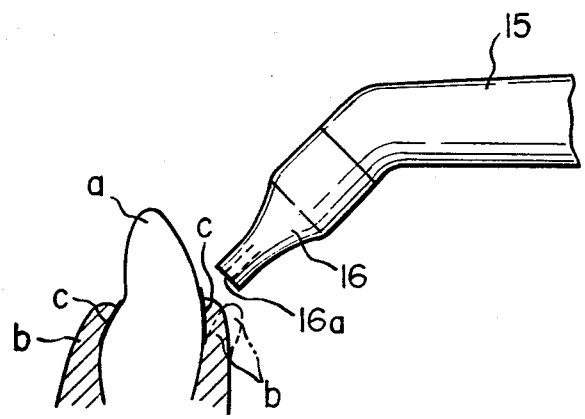
FIG. 5 is a schematic side view showing the ejection nozzle as directed to the gum pocket of a tooth.

The present inventor, however, has found out that, when jet water is caused to act on the surface of teeth at the gum pocket in the form of spray and being carried on the jet air, such jet air, even under a relatively low ejecting pressure, readily blows in between the tooth a at the gum pocket and the gingiva b to be sufficiently separated from the tooth a as shown by a double dots-and-dash line in FIG. 5, as the consequence of which the jet water can sufficiently act on the thus exposed surface of teeth at the gum pocket, in the form of spray jet, whereby scaling and removal of sordes and tartars c adhered on the teeth can be effectively done due to such jet air and the spray jet water. On the basis of such observation, the present invention has been completed. Incidentally, the gingiva b which has been separated from the surface of teeth will again be closed due to its elasticity as soon as the ejection of the pressurized air is ceased.

The air to be ejected from the nozzle should practically have a pressure of from 1 to 2 $kg/cm^2$, and be in an ejecting quantity of from 6 to 9 l/min. With a pressure not reaching 1 $kg/cm^2$ and an ejecting quantity not reaching 6 l/min., the gingiva b cannot effectively be separated from the tooth a at the gum pocket and the operating pressure of the spray jet water becomes also low with the result that no effective scaling of sordes and tartars can be carried out. On the other hand, with the pressure of above 2 $kg/cm^2$ and the ejecting quantity of above 9 l/min., impingement of the jet air and the spray jet water onto the tooth a, the gingiva b, and every other part of the mouth interior becomes excessively strong. Moreover, it is not necessary to increase the ejecting pressure of the air and water to such a strong level for attaining the sufficient separation of the gingiva b from the tooth and the effective removal or scaling of the sordes and tartars by the spray jet water. Rather, such increased pressure is wasteful for the particular purpose.

The ejecting quantity of the spray jet water to be ejected on the abovementioned jet air stream should appropriately be from 10 to 30 cc/min. or so. With the ejecting quantity not reaching 10 cc/min., no effective scaling of the sordes and tartars c can be attained, because of extremely small quantity of the spray jet water to act on the surface of teeth. On the other hand, the quantity of water exceeding 30 cc/min. is unnecessarily large for the effective scaling of the sordes and tartars c, hence it is wasteful.

In general, the scaling of the sordes and tartars on the surface of teeth for a single scaling operation can be effectively completed by causing the abovementioned mixed stream of jet air and spray jet water to act uniformly throughout the mouth interior and on the gum pocket of each tooth for about one minute, whereby the spaces between the adjacent teeth can be cleaned very satisfactorily, and food residues, various germs, etc. can also be removed effectively. In addition, the pressure of these jet air and spray jet water serves for massaging the gingiva. The quantity of water to collect in the mouth during the scaling and washing-out operation is at most as small as 10 to 30 cc, which may therefore be kept within the mouth until completion of the scaling and washing for a single cleaning operation, and thereafter it may be spat outside, which conveniently facilitates handling of the nozzle hand-piece.

With a view to enabling those persons skilled in the art to put the present invention into practice, the following preferred examples are explained in reference to the accompanying drawings.

Referring first to FIG. 1, illustrating a portable type device for scaling and washing-out sordes and tartars from the surface of teeth at the gum pocket, which can be used conveniently at home and on one's journey as well, a reference numeral 1 designates a small-sized casing, designed to have an arbitrary external shape, for the main body of the device which can be freely carried by gripping a handle 2 fixedly provided on the main body casing 1. Within this casing, there are housed a small-sized compressor 3 such as, for example, a small-sized diaphragm pump of 30 to 50 W. A numeral 4 refers to a plug and a cord for feeding electric current to the compressor 3, the plug being inserted into a plug receptacle for a commercial power source. Reference numerals 5 and 6 denote respectively a power source switch and a pilot lamp disposed on the top surface of the carrying handle 2 in this embodiment. When the switch 5 is turned on, the lamp 6 is lit and the compressor 3 starts to operate. A numeral 7 refers to a dial for regulating pressure of air, which is disposed on the top surface part of the main body casing 1 of the device in this embodiment. By manipulating this dial in rotation, the pumping operation of this compressor 3 is controlled to be either high or low, whereby pressure and outlet quantity of the compressed air from an air outlet tube 8 can be adjusted arbitrarily.

A reference numeral 9 designates conduit tube for compressed air, which is flexible butless collapsible. The tube is connected at its one end with the air outlet tube 8, and is extended at its other end outward of the main body casing 1 of the device in an appropriate length, e.g., 1 m or so.

A numeral 10 refers to a water container of a small capacity of about 50 to 100 cc, which is removably housed in a lateral recess 11 formed in one side of the main body casing 1 of the device.

A numeral 12 refers to a flexible thin tube for conducting water therethrough, which is inserted in the abovementioned pressurized air conduit tube 9. One end 12a of this water conduit tube 12 is drawn outside of the compressed air conduit tube 9 through the tube wall at a position closer to the top ceiling wall of the abovementioned lateral recess 11 for accommodating the water container 10, and is extended through the center part of the ceiling wall of the lateral wall toward the bottom surface thereof. At the time of housing this water container filled with water W (including warm water at an appropriate temperature, water or warm water added with tooth wash or other medicinal substances, and so forth) into this recess 11, the end part 12a of the water conduit tube extending into this lateral recess 11 is properly flexed so as to be put inside the water container 10, after which it is inserted into the recess 11.

A reference numeral 13 represents a hand-piece for the ejection nozzle, the details of which are shown in FIG. 2 which is an enlarged longitudinal cross-sectional view. In this ejection nozzle hand-piece, a numeral 14 refers to a hollow gripping handle, a numeral 15 refers to a beaked tube of an appropriate length with a nozzle mouthpiece 16 being screw-connected with the free end of the beaked tube 15. The other end of this tube 15 has a male-threaded part 15a formed on its outer periphery, which is screwed into a female threaded part 14a formed on the inner periphery of the front end of the abovementioned hollow gripping handle 14, in such a manner that the beaked tube 15 may be joined with the gripping handle in a freely removable manner. In their joined state, both hollow gripping handle 14 and beaked tube 15 are made mutually communicative.

A numeral 17 refers to a thin tube which is inserted to pass through the bore of the gripping handle 14 and the beaked tube 15. The rear end 17b of this thin tube 17 is held in a cylindrical holding die 18 which is fitted in the rear end of the hollow gripping handle 14, while the front end 17a thereof is situated at a position near the screw-connected part of the nozzle mouthpiece 16 at the front tip end of the beaked tube 15.

The compressed air conduit tube 9 is fitted at its front tip end into the cylindrical holding die 18 at the rear end of the hollow gripping handle 14 of the abovementioned ejection nozzle hand-piece 13, and, by screwing a cap screw 19 into this rear end of the gripping handle, the compressed air conduit tube is communicatively connected with the gripping handle 14. Further, the front tip end of the water conduit tube 12 inserted into the compressed air conduit tube 9 is fittingly connected with the rear end of the thin tube 17 which has been disposed in the bore of the gripping handle 14 of the abovementioned hand-piece 13 and the beaked tube 15 in such a manner that it may be communicative with the thin tube 17.

When the power source switch 5 is turned on, the pressurized air is supplied from the compressor 3 to the nozzle mouthpiece 16 by way of the air outlet tube 8, the air conduit tube 9, the bore of the gripping handle 14 of the hand-piece 13, and the bore of the beaked tube 15, whereby the compressed air is ejected from the nozzle 16a of the nozzle mouthpiece 16 as the jet air. On the other hand, with ejection of the jet air from this nozzle 16a, the pressure of the air in the front end 17a of the thin tube 17 situated at the neighboring position where the nozzle mouthpiece 16 is screwed within the beaked tube 15 becomes negative. By this negative pressure, the water W in the water container 10 is sucked up consecutively into the water conduit tube 12 from mouth of the rear end 12a thereof on the same principle as the sprayer or the atomizer, passes through the thin tube 17, flows out of the mouth of the front end 17a of the thin tube 17, and is ejected as the jet spray water from the nozzle 16a of the nozzle mouthpiece 16 together with the jet air.

By appropriately mnipulating the dial 7 in rotation to control the pumping operation of the compressor 3, it is possible to regulate the pressure and the quantity of jet air to be ejected from the nozzle mouthpiece. Also, by appropriately manipulating the beaked tube 15 in rotation with respect to the gripping handle 14 in the forward-moving direction or in the rearward-moving direction, the front tip end 17a of the thin tube 17 changes its position within the beaked tube 15 to thereby change the negative pressure at the front tip end 17a thereof with the consequence that the ejecting quantity of the jet spray water can be adjusted.

Figure 3:
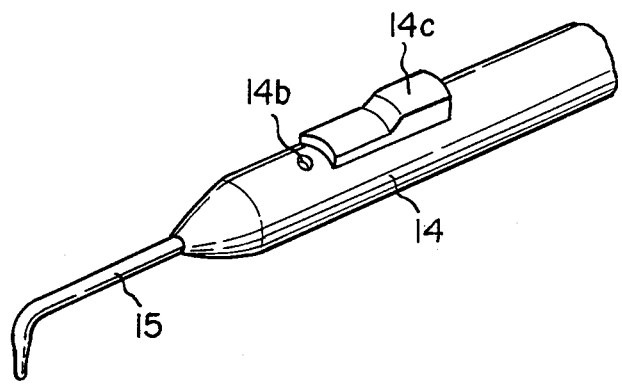
FIG. 3 is a perspective view showing a modified hand-piece for the ejection nozzle, in which a control switch is provided.

As shown in FIG. 3, by the formation of the pressurized air discharging port 14b in one part of the gripping handle 14, and by providing an opening and closing switch 14c for the discharging port 14b, it becomes possible to eject spray jet water from the nozzle 16 while the discharge port 14b is being closed, and to stop it from ejection while the discharge port is being opened.

In the above-described state, wherein the ejecting pressure of the jet air from the nozzle mouthpiece 16 is set in a range of from 1 to 2 kg/cm$^2$, the ejecting quantity of the jet air is set in a range of from 6 to 9 l/min., and the ejecting quantity of the jet spray water is set in a range of from 10 to 30 cc/min., the jet air and the spray jet water are evenly ejected together from the nozzle mouthpiece 16 to the gum pocket of each individual tooth for about one minute, whereby the sordes and tartars c on the surface of teeth at the gum pocket can be effectively removed.

Figure 4:
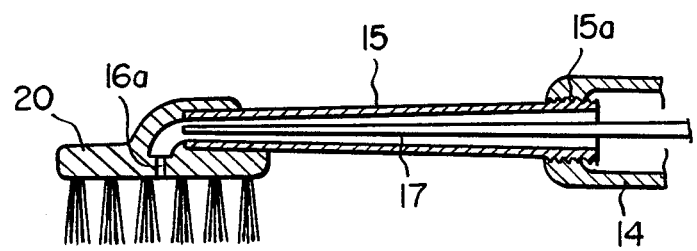
FIG. 4 is a longitudinal cross-section view showing a different embodiment of the ejection nozzle.

As a modification of the device according to the present invention, a tooth brush 20 is provided at the tip end of the beaked tube 15, as shown in FIG. 4, in which the ejecting nozzle 16a for both jet air and spray jet water is formed, whereby the jet air and the spray jet water can be ejected from the nozzle 16a to be impinged onto the teeth, while they are being brushed.

It is furthermore feasible that the water container 10 is made in a small cassette type container which is freely attachable to and detachable from the gripping handle 14 of the ejection nozzle hand-piece 13, or it can be provided in a form, wherein the water container is incorporated in the gripping handle per se.

As has been described in the foregoing, the device for scaling and washing-out sordes and tartars from the surface of teeth according to the present invention is capable of effectively removing the sordes and tartars accumulated on the surface of teeth at the gum pocket with a small quantity of water and without causing any pain and disagreeable feeling on the part of a user of such device, hence the intended object can well be achieved.

What is claimed is:

1. A device for scaling sordes and tartars on the surface of teeth at the gum pocket, which comprises:
    a hand-piece including an ejection nozzle;
    a compressor for feeding compressed air to said ejection nozzle at one end of said hand-piece;
    a conduit pipe for transporting the compressed air;
    a water sump;
    a conduit for leading water from said water sump to said ejection nozzle;
    said compressed air being ejected from said ejecting nozzle of the hand-piece under a pressure of from 1 to 2 kg/cm$^2$ and in an ejecting quantity of from 6 to 9 l/min.; and
    venturi ejecting means for ejecting said water together with said compressed air in an ejecting quantity of from 10 to 30 cc/min. in the form of a pressurized air spray jet for exposing the surface of teeth at the gum pocket by separating the gingival from the teeth.

2. A scaling device as set forth in claim 1, wherein a pressurized air discharging port and a switch for opening and closing said discharge port are provided in one part of said hand-piece, ejection of the pressurized air and water from said nozzle being controllable by operation of said switch.

3. A scaling device according to claim 1, wherein a tooth brush is attached at the tip end of the beaked tube, and pressurized air and water are ejected from an ejection nozzle formed in one part of said tooth brush.

* * * * *

UNITED STATES PATENT AND TRADEMARK OFFICE
CERTIFICATE OF CORRECTION

PATENT NO.  : 4,906,187
DATED       : March 6, 1990
INVENTOR(S) : Haruichi Amadera It is certified that error appears in the above-identified patent and that said Letters Patent is hereby corrected as shown below:

On the title page, in item [75], add the following additional inventor:
--Koichi Okano, Shiga-ken, Japan--

Signed and Sealed this

Thirtieth Day of June, 1992

Attest:

DOUGLAS B. COMER

*Attesting Officer*     *Acting Commissioner of Patents and Trademarks*